US006730813B2

(12) United States Patent
Hitzler et al.

(10) Patent No.: US 6,730,813 B2
(45) Date of Patent: May 4, 2004

(54) METHOD FOR PRODUCING N-(PHOSPHONOMETHYL) GLYCINE

(75) Inventors: Martin Hitzler, Tacherting (DE); Franz Thalhammer, Trostberg (DE); Benedikt Hammer, Tacherting (DE)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 10/204,037

(22) PCT Filed: Feb. 16, 2001

(86) PCT No.: PCT/EP01/01749
§ 371 (c)(1), (2), (4) Date: Aug. 16, 2002

(87) PCT Pub. No.: WO01/60830
PCT Pub. Date: Aug. 23, 2001

(65) Prior Publication Data
US 2003/0050503 A1 Mar. 13, 2003

(30) Foreign Application Priority Data
Feb. 19, 2000 (DE) .......................... 100 07 702

(51) Int. Cl.⁷ ................................................ C07F 9/30
(52) U.S. Cl. ...................................................... 568/17
(58) Field of Search ................... 562/8, 11, 16, 562/17

(56) References Cited

U.S. PATENT DOCUMENTS

| | | | |
|---|---|---|---|
| 3,288,846 A | | 11/1966 | Irani et al. |
| 3,969,398 A | * | 7/1976 | Hershman ............... 562/17 |
| 4,147,719 A | * | 4/1979 | Franz ...................... 562/17 |
| 4,579,689 A | | 4/1986 | Hershman et al. |
| 4,582,650 A | | 4/1986 | Felthouse |
| 4,851,131 A | | 7/1989 | Grabiak et al. |
| 5,087,740 A | | 2/1992 | Smith |
| 5,091,561 A | * | 2/1992 | Riley et al. ............. 562/17 |
| 5,179,228 A | * | 1/1993 | Martin Ramon et al. ... 562/17 |
| 5,898,082 A | | 4/1999 | Hodgkinson |
| 5,948,938 A | | 9/1999 | Nakano et al. |
| 5,962,729 A | * | 10/1999 | Hayden et al. .......... 562/17 |
| 6,365,772 B1 | * | 4/2002 | Cullen et al. ........... 562/17 |
| 6,586,621 B2 | * | 7/2003 | Leiber et al. ........... 562/17 |
| 2002/0068836 A1 | | 6/2002 | Haupfear et al. |

FOREIGN PATENT DOCUMENTS

| | | |
|---|---|---|
| DE | 199 38 622 A1 | 2/2001 |
| EP | 0 323 821 A1 | 7/1989 |
| EP | 0 323 821 B1 | 6/1992 |
| EP | 0 413 672 B1 | 2/1995 |
| WO | WO 96-40592 A1 | 12/1996 |
| WO | WO 97/05149 A1 | 2/1997 |
| WO | WO 01/66508 A2 | 9/2001 |

OTHER PUBLICATIONS

Anonymous, "Recycle Process", *Research Disclosure*, Kenneth Mason Publications Ltd., Dec. 1997, No. 404, pp. 942, 40466.

* cited by examiner

Primary Examiner—Jean F. Vollano
(74) Attorney, Agent, or Firm—Senniger, Powers, Leavitt & Roedel; Joseph A. Schaper

(57) ABSTRACT

The invention relates to a method for producing N-(phosphonomethyl)glycine involving the following steps: (a) oxidizing N-(phosphonomethyl)iminodiacetic acid (PMIDA) with peroxides or oxygen in an aqueous medium and in the presence of a heterogeneous catalyst at a temperature ranging from 50 to 150° C.; (b) subsequently separating the solid catalyst out of the aqueous reaction suspension of step (a); (c) concentrating the clear reaction solution from step (b), especially by evaporation, and; (d) separating the N-(phosphonomethyl)glycine out of the concentrated reaction solution from step (c), especially by filtration. According to the invention, the aqueous reaction solution from step (d) (mother liquor) is returned with small amounts of N-(phosphonomethyl)glycine and byproducts to step (b) (catalyst separation) and/or to step (c) (concentration). This results in distinctly increasing the yield with a constant product purity and in noticeably reducing the amount of mother liquor.

18 Claims, No Drawings

METHOD FOR PRODUCING N-(PHOSPHONOMETHYL) GLYCINE

This application is a 371 of PCT/EP01/01749 filed Feb. 16, 2001, now WO 01/60830.

The present invention relates to a method for the production of N-(phosphonomethyl)glycine (PMG), which facil-itates a very effective and economical recycling of waste water streams from; the preceding processes for the production of N-(phosphonomethyl)glycine starting from N-(phosphonomethyl)imino-diacetic acid (PMIDA).

N-(Phosphonomethyl)glycine is a highly effective herbicide with full-systemic mode of action known in agriculture under the name of Glyphosate. It overcomes annual and perennial weeds and grass weed species. The application is multifarious and has acquired world-wide enormous economic importance.

According to the stand of technology, there are several manufacturing processes for the production of glyphosate. For example, in U.S. Pat. No. 3,950,402; EP 0 472 693 B1; U.S. Pat. No. 4,147,719 Monsanto describes methods for the oxidation of PMIDA with oxygen or peroxides such as hydrogen peroxide in the presence of a precious metal bound to activated carbon (Pt/C, Pd/C, Rh/C). In other methods, the conversion is carried out only with activated carbon as catalyst (EP-A 0 162 035; DE-OS 30 17 518; U.S. Pat. No. 3,969,398; WO 96/38455; WO 96/27602). Patent ES 9202254 describes a method for the conversion of PMIDA in the presence of an ion exchange resin—preferably a cation exchanger in a protonated form—with peroxides.

The described methods, even if they are highly efficient, have all a common disadvantage that in the production of glyphosate large quantity of waste water are accumulated. Typically, in the described processes an aqueous solution or suspension of N-(phosphonomethyl)iminodiacetic acid is converted, with peroxides or oxygen in the presence of a hetero-geneous catalyst, to glyphosate. The use of heterogeneous catalysts stipulates that after the reaction the product has to be dissolved in the solvent, since otherwise during the separation of the catalyst the product would be separated along. However, glyphosate is only slightly soluble in water (5° C.: 0.8%, 20° C.: 1.1%, 95° C.: 6.5%); the solubility in organic solvents is even much lower. Consequently, for these processes large volumes of water are required.

After the separation of the catalyst, the reaction solution has to be concentrated for isolating the product, whereby a condensate-waste water stream is formed (in the following named condensate). Then the product is filtered or centrifuged while a filtrate-waste water stream is formed (in the following named filtrate).

The condensate contains, as substantial impurities, formaldehyde and formic acid. The contamination profile of the filtrate consists of a number of by-products and cleavage products—mostly phosphorus-containing compounds. Typically, a filtrate still contains 1 to 4% by weight glyphosate. Because of the components, the disposal presents a problem, since several of the components have herbicidal properties. Moreover, due to the components, neither the condensate nor the filtrate can be recycled as a reaction medium. Therefore, it is of interest to minimize the residual quantities of glyphosate in the filtrate and to reduce the quantities of the filtrate. The advantages are in a higher efficiency of the production process, in a lowering of the disposal costs, and in the protection of the environment.

The recovery of glyphosate from the filtrate is described in WO 97/05149. The method is based on the separation of a difficultly soluble complexes which glyphosate forms with iron(III) salts (also: Ca, Mg, Al). By a variation of the pH value, glyphosate can be set free from the complex and can be isolated or can be recycled to the process. However, this type of recovery is very costly.

EP 0 323 821 B1 discloses a treatment of the filtrate from the glyphosate processes. For this purpose, after separation from the main quantity of the product, the remaining quantities of PMIDA, glyphosate, and other phosphonic acids (e.g., aminomethanephosphonic acid, briefly AMPS) remaining in the filtrate are destroyed with oxygen on transition metal catalysts (e.g., Mn, Co, Fe) typically at 35 bar and 120° C. (>85% after 6 hours). However, the destruction of the components is connected with a very high technical process cost and therewith in two ways very costly.

Consequently, the present invention has for its object to develop an improved method for the production of glyphosate, which at least partly avoids the indicated disadvantages according to the state of technology and recovers the available substances contained in the mother liquor, without higher technical costs. Moreover, a decrease of the waste water streams formed in the process should be achieved.

This problem is solved by a method for the production of N-(phosphonomethyl)glycine (glyphosate) by (a) oxidation of N-(phosphonomethyl)iminodiacetic acid with peroxides or oxygen in an aqueous medium in the presence of a heterogeneous catalyst, (b) followed by the separation of the catalyst from the aqueous reaction suspension from stage (a), (c) concentration of the clear reaction solution from stage (b), especially by evaporation, and (d) separation of N-(phosphonomethyl)glycine from the concentrated reaction solution from stage (c), especially by filtration, which is characterized in that the aqueous reaction solution from stage (d) (mother liquor) is recycled to stage (b) (catalyst separation) and/or stage (c) (concentration).

Surprisingly, we discovered that the residual quantity of glyphosate in the mother liquor as well as the volume of the mother liquor itself can be significantly reduced when the latter is recycled to stage (b) and/or stage (c) and simultaneously glyphosate can be isolated in a high yield at unchanged high purity, by means of a method of the invention at a low technical expenditure.

According to the present invention, the method comprises at least four stages. In the first stage (a) N-(phosphonomethyl)iminodiacetic acid is oxidized in aqueous solution, whereby the reaction conditions can vary within very broad limits. Peroxides such as hydrogen peroxide or oxygen-containing gases as well as their mixtures can be used as oxidation agents. Likewise, the choice of the catalyst can be optional. Applied are, e.g., precious metal catalysts such as palladium, platinum, and rhodium, especially on activated carbon, pure activated carbon catalysts or pure precious metal catalysts. A choice of activated carbon is described, for example, in the following patents: EP-A 162 035, U.S. Pat. No. 3,969,398, WO 96/38 455, WO 96/27 602 and DE-OS 30 17 518. The reaction conditions for carrying out the oxidation reaction can be varied within broad limits. For example, reaction stage (a) is customarily carried out in aqueous medium at temperatures between 50 and 150° C., especially between 50 and 100° C., under pressure from 0.5 to 50 bar, and catalyst portions from 2 to 50% by weight based on the charged quantity of PMIDA. In the conversion with peroxides the molar ratio of PMIDA to peroxide is preferably adjusted to between 1:1.5 and 1:5. When the oxidation is carried out with an oxygen-containing gas, as a rule the gas is conveyed under pressure through the reaction mixture. The concentration of the reaction components in aqueous suspension can be varied in broad limits and is preferably adjusted to 1 to 30% by weight based on the charged N-(phosphonomethyl)iminodiacetic acid. The reaction times can vary depending on the reaction conditions and can move in a range from a few minutes to several hours.

In the following stage (b) the solid catalyst is separated from the aqueous reaction stage (a) which can occur according to known methods such as filtration or centrifugation. The separation is preferably done by filtration in a temperature range from 50 to 100° C. possibly also under pressure. The separated catalyst can then be recycled directly into reaction stage (a).

After the separation of the catalyst, the clear reaction solution from stage (b) is concentrated in stage (c) for example, by evaporation, whereby the concentration step is preferably carried out at temperatures from 20 to 90° C., and in vacuum from 20 to 700 mbar to a preferred water content from 10 to 70% by weight.

Subsequently, in stage (d) the separation of N-(phosphonomethyl)glycine from the concentrated reaction solution from stage (c) is carried out preferably by filtration, but also by centrifugation. According to a preferred mode of operation, the product (glyphosate) can be subjected to a purification step with water, and the wash water can be combined with the aqueous reaction solution from stage (d) (mother liquor).

It should be considered as invention essential that the mother liquor (aqueous reaction solution from stage (d)) which usually contains small quantities of glyphosate (1 to 4% by weight) and by-products, at least partly is recycled in stage (b) (catalyst separation) and/or stage (c) (concentration).

Since the oxidation stage (a) for the production of glyphosate, as a rule, is carried out batch-wise, the proposed recycling according to the invention is conducted in such a form that the mother liquor is totally or partly used in the processing of the subsequent batch either in stage (b) and/or stage (c). In this manner the mother liquor is integrated in a cyclic process, which in certain cases can be repeated as frequently as considered practical, since no noticeable product deterioration can be detected even after 5 to 10 reaction cycles.

In the method of the present invention the following advantages arise which, according to the previous state of technology, could not be expected:

An Increased Yield at Constant Product Purity:
  The mother liquor represents a saturated solution of the product. In the recycling the yield increases by the remaining quantity of the product present in the filtrate, since the new mother liquor is also a saturated solution of the product. Surprisingly, the purity of the product is maintained even after several recyclings of the mother liquor into the process.

Reduction of the Filtrate Quantity:
  Since the reaction suspension is always concentrated to the same quantity of the reaction volume, the same quantity of the mother liquor per charge is formed. Consequently, one has a process-internal concentration without additional requirement for equipment and without increased costs. The total quantity of the mother liquor obtained as waste water is reduced by the number of recyclings.

The indicated advantages lead to a cost decrease in two ways: by lowering the cost of glyphosate due to the increased yields and by saving in expenses for the mother liquor disposal.

The following examples should illustrate the invention.

EXAMPLES

The following three examples with comparison examples refer to a process for the oxidation of PMIDA in aqueous solution with hydrogen peroxide in the presence of an activated carbon catalyst, as described for example in the PCT applications WO 96/38455 and WO 97/27602. The examples are not limiting in any way. They rather describe the basic method for recycling the mother liquor to the process.

Example 1 (B1)
Recycling of the Mother Liquor in Stage (c) (Concentration Step)

A filtrate B1-1 after separation of the product of an oxidation process at 60 to 65° C. crystallized from the concentrated reaction mixture shows the typical composition of the components in Table 1 (compare Example 1 (8) of the PCT application WO 96/27602). The oxidation reaction is repeated, whereby the entire filtrate B1-1, according to the recycling process of the invention, is recycled to stage (c) (concentration) without separating a part of the stream. The composition of filtrate B1-6 after the fifth recycling is also presented in Table 1.

TABLE 1

| component | filtrate B1-1 without recycling (%) | filtrate B1-6 after fifth recycling (%) |
|---|---|---|
| PMG[1] | 1.2 | 1.3 |
| PMIDA[2] | <0.2 | <0.2 |
| AMPS[3] | 0.3 | 0.5 |
| N-Me-PMG[4] | 0.9 | 1.3 |
| phosphate | 0.2 | 1.0 |
| formaldehyde | 0.5 | 1.0 |
| formate | 3.7 | 12.4 |

Acronyms explanation:
[1]PMG N-(phosphonomethyl)glycine = glyphosate
[2]PMIDA N-(phosphonomethyl)imino-diacetic acid
[3]AMPS aminomethanephosphonic acid
[4]N-Me-PMG N-Methyl-N-(phosphonomethyl)glycine

TABLE 2

| Comparison Example* from Example 1(8) of the PCT Application WO 96/27602 | | |
|---|---|---|
| | PMG purity (%) | PMG Yield (%) |
| Comparison example* (without mother liquor recycle) | 98.2 | 85.9 |
| Example according to the invention with 5 mother liquor recyclings to stage (c) - concentration | 98.9–98.3 | 87.6–92.0 |
| Average for example according to the invention with 5 mother liquor recyclings to stage (c) - concentration | 98.5 | 89.9 |

The purity and the yields of glyphosate with recycling of the filtrate are compared with the data of the examples without recycling of the filtrate are presented in Table 2. By recycling the filtrate according to the invention the product is obtained with unchanged purity, the same as in the comparison example. Moreover, the yield of glyphosate is increased, and the volume of the filtrate is decreased sixfold.

Example 2 (B2)
Recycling of the Mother Liquor in Stage c) (Concentration)

Filtrate B2-1, after separation of the product of an oxidation process at 90–95° C., crystallized from the concentrated reaction mixture, shows the typical composition of the components (compare Example 5(7) of the PCT application WO 96/27602) presented in Table 3. The oxidation reaction is repeated, whereby the entire filtrate B2-1, according to the recycling process of the invention, is recycled into stage c) (concentration) without separation of a partial stream. The composition of filtrate B2-6 after the fifth recycling and B2-10 after the ninth recycling are also included in Table 3.

TABLE 3

| component | filtrate B2-1 without recycling (%) | filtrate B2-6 after fifth recycling (%) | filtrate B2-10 after ninth recycling (%) |
|---|---|---|---|
| PMG | 1.2 | 4.3 | 5.4 |
| PMIDA | <0.2 | <0.2 | <0.2 |
| AMPS | 0.4 | 4.1 | 4.7 |
| N-Me-PMG | 1.5 | 4.5 | 5.6 |
| phosphate | 0.4 | 4.4 | 6.8 |
| formaldehyde | 0.5 | 1.0 | 1.0 |
| formate | 3.7 | 6.4 | 6.6 |

The purity and the yields of glyphosate with recycling of the filtrate are compared with the comparison example without recycling of the filtrate are compiled in Table 4. By recycling the filtrate according to the invention the product is obtained which has unchanged purity, the same as in the comparison example. Moreover, the yield of glyphosate is increased, and the quantity of the filtrate is decreased six- and ten-fold, respectively.

TABLE 4

Comparison Example* from Example 5(7) of the PCT Application WO 96/27602

| | PMG purity (%) | PMG Yield (%) |
|---|---|---|
| Comparison example* (without mother liquor recycle) | 98.4 | 79.2 |
| Example according to the invention with 5 mother liquor recyclings to stage (c) - concentration | 99.6–97.0 | 85.1–91.0 |
| Average for example according to the invention with 5 mother liquor recyclings to stage (c) - concentration | 98.5 | 89.9 |
| Example according to the invention with 9 mother liquor recyclings to stage (c) - concentration | 99.6–96.2 | 85.1–92.6 |
| Average for example according to the invention with 9 mother liquor recyclings to stage (c) - concentration | 98.0 | 90.0 |

Example 3 (B3)
Recycling the Mother Liquor to Stage b) (Catalyst Separation)

Filtrate B3-1, after separation of the product of oxidation process at 90–95° C. and crystallized from the concentrated reaction mixture, shows the typical composition of the components (compare Example 5(7) of the PCT application WO 96/27602) compiled in Table 5. The oxidation reaction is repeated, whereby the entire filtrate B3-1, according to the recycling process of the invention, without separating a part of the stream, is returned to stage b) (catalyst separation). The composition of filtrate B3-4 after third recycling is also presented in Table 5.

TABLE 5

| component | filtrate B3-1 without recycling (%) | filtrate B3-4 after third recycling (%) |
|---|---|---|
| PMG | 2.5 | 3.7 |
| PMIDA | 0.3 | 1.8 |
| AMPS | 0.2 | 0.8 |
| N-Me-PMG | 0.9 | 2.2 |
| phosphate | 0.4 | 1.8 |
| formaldehyde | 0.2 | 0.3 |
| formate | 2.9 | 6.1 |

TABLE 6

Comparison Example* from Example 5(7) of the PCT Application WO 96/27602

| | PMG purity (%) | PMG Yield (%) |
|---|---|---|
| Comparison example* (without mother liquor recycle) | 98.4 | 79.2 |
| Initial charge of example according to the invention | 97.7 | 76.9 |
| Example according to the invention with 3 mother liquor recyclings to stage (d) - catalyst separation | 97.1–97.4 | 86.2–90.3 |
| Average for example according to the invention with 3 mother liquor recyclings to stage (d) - catalyst separation | 97.4 | 90.0 |

The purity and the yields of glyphosate with recycling the filtrate contrasted with the comparison example without recycling the filtrate are shown in Table 6. By recycling the filtrate according to the invention, the product is obtained with about the same purity as in the comparison example. In addition, the yield of glyphosate is significantly increased and the volume of the filtrate is reduced four-fold.

What is claimed is:

1. A method for the production of N-(phosphonomethyl) glycine comprising:
   (a) oxidizing N-(phosphonomethyl)iminodiacetic acid with peroxide or an oxygen-containing gas in an aqueous medium in the presence of a heterogeneous catalyst to form an aqueous reaction suspension,
   (b) separating the catalyst from the aqueous reaction suspension from stage (a) to form a reaction solution,
   (c) concentrating the reaction solution from stage (b),
   (d) separating N-(phosphonomethyl)glycine from the concentrated reaction solution from stage (c) to form a mother liquor, and
   (e) recycling at least a portion of the mother liquor from stage (d) to stage (b) and/or to stage (c).

2. A method according to claim 1 wherein the N-(phosphonomethyl)iminodiacetic acid is oxidized with an oxygen-containing gas in stage (a).

3. A method according to claim 2 wherein activated carbon is used as catalyst in stage (a).

4. A method according to claim 2 wherein the catalyst in stage (a) comprises a precious metal selected from the group consisting of palladium, platinum and rhodium fixed on a carrier material.

5. A method according to claim 2 wherein the catalyst in stage (a) is used in a quantity from 2 to 50% by weight, based on the quantity of the charged N-(phosphonomethyl) iminodiacetic acid in the aqueous medium.

6. A method according to claim 1 wherein the N-(phosphonomethyl)iminodiacetic acid is oxidized with peroxide in stage (a) and the molar ratio of N-(phosphonomethyl)iminodiacetic acid to peroxide is adjusted to a range from 1:1.5 to 1:5.

7. A method according to claim 2 wherein the oxidation in stage (a) is carried out at a temperature of from 50 to 150° C.

8. A method according to claim 2 wherein the oxidation in stage (a) is carried out at a pressure of from 0.5 to 50 bar.

9. A method according to claim 2 wherein the concentration of the charged N-(phosphonomethyl)iminodiacetic acid in the aqueous medium in stage (a) is adjusted to 1 to 30% by weight.

10. A method according to claim 2 wherein the catalyst in stage (b) is separated from the aqueous reaction suspension by filtration.

11. A method according to claim 10 wherein the filtration in stage (b) is carried out at a temperature of from 50 to 100° C.

12. A method according to claim 2 wherein the reaction solution in stage (c) is concentrated by evaporation.

13. A method according to claim 2 wherein the reaction solution is concentrated in stage (c) to a water content from 10 to 70% by weight.

14. A method according to claim 2 wherein the concentration of the reaction solution in stage (c) is carried out at a temperature of from 20 to 90° C. and in a vacuum from 20 to 700 mbar.

15. A method according to claim 2 wherein N-(phosphonomethyl)glycine in stage (d) is separated from the concentrated reaction solution by centrifugation.

16. A method according to claim 2 wherein the mother liquor recycled from stage (d) contains small quantities of N-(phosphonomethyl)glycine and by-products.

17. A method according to claim 2 wherein the oxidation stage (a) is carried out in a batch-wise manner and at least a portion of the mother liquor recycled from stage (d) is used in the working up of the following batch.

18. A method according to claim 17 wherein the recycling of the mother liquor is conducted in 5 to 10 reaction cycles.

* * * * *

UNITED STATES PATENT AND TRADEMARK OFFICE
CERTIFICATE OF CORRECTION

PATENT NO. : 6,730,813 B2
DATED : May 4, 2004
INVENTOR(S) : Martin Hitzler

It is certified that error appears in the above-identified patent and that said Letters Patent is hereby corrected as shown below:

Column 6,
Lines 47-50, "(c) concentrating the reaction solution from stage (b), (d) separating N-(phosphonomethyl)glycine from the concentrated reaction solution from stage (c) to form a mother liquor, and" should read -- (c) concentrating the reaction solution from stage (b) to form a concentrated reaction mixture comprising crystalline N-(phosphenomethyl) glycine product and a mother liquor, (d) separating crystalline N-(phosphonomethyl)glycin product from the concentrated reaction mixture from stage (c) and --.
Lines 63-65, "(a) is used in a quantity from 2 to 50% by weight, based on the quantity of the charged N-(phosphonomethyl)iminodiacetic acid in the" should read f --(a) is present in the aqueous medium at a concentration of from 2 to 50% by weight, based on the weight of N-(phosphonomethyl)iminodiacetic acid charged to the --.

Column 7,
Lines 10-11, "of the charged N-(phosphonomethyl)iminodiacetic acid in the aqueous medium in stage (a) is adjusted to 1 to 30%" should read -- of N-(phophonomethyl) iminodiacetic acid charged to the aqueous medium in stage (a) is 1 to 30% --.

Column 8,
Lines 8-10, "wherein N-(phosphonomethyl)glycine in stage (d) is separated from the concentrated reaction solution by" should read -- wherein crystalline N-(phosphonomethyl) glycine product in stage (d) is separated from the concentrated reaction mixture by --.
Lines 15-16, "(d) is used in the working up of the following batch." should read -- (d) is used in the processing of a subsequent batch either in stage (b) and/or stage (c) .-- .

Signed and Sealed this

Fifth Day of October, 2004

JON W. DUDAS
*Director of the United States Patent and Trademark Office*